(12) United States Patent
McGuinness et al.

(10) Patent No.: US 10,241,066 B2
(45) Date of Patent: Mar. 26, 2019

(54) MICROFLUIDIC SENSING DEVICE

(71) Applicant: Hewlett-Packard Development Company, L.P., Houston, TX (US)

(72) Inventors: Nicholas Matthew Cooper McGuinness, San Diego, CA (US); Melinda M. Valencia, Chula Vista, CA (US); Manish Giri, Corvallis, OR (US); Chantelle Elizabeth Domingue, Corvallis, OR (US); Jeremy Sells, Albany, OR (US); Matthew David Smith, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 11 days.

(21) Appl. No.: 15/112,639

(22) PCT Filed: Jan. 30, 2014

(86) PCT No.: PCT/US2014/013748
§ 371 (c)(1),
(2) Date: Jul. 19, 2016

(87) PCT Pub. No.: WO2015/116083
PCT Pub. Date: Aug. 6, 2015

(65) Prior Publication Data
US 2016/0334323 A1    Nov. 17, 2016

(51) Int. Cl.
*G01N 27/06*       (2006.01)
*G01N 15/02*       (2006.01)
(Continued)

(52) U.S. Cl.
CPC ........ *G01N 27/06* (2013.01); *B01L 3/502715* (2013.01); *G01N 15/0266* (2013.01);
(Continued)

(58) Field of Classification Search
CPC .......... G01N 15/1031; G01N 15/0266; G01N 27/12; G01N 2015/1006; G01N 27/06; G01N 15/026
(Continued)

(56) References Cited

U.S. PATENT DOCUMENTS 4,420,720 A    12/1983  Newton et al.
5,965,410 A    10/1999  Chow et al.
(Continued)

FOREIGN PATENT DOCUMENTS

CN        102360025 A      2/2012
JP        2013015498       1/2013
(Continued)

OTHER PUBLICATIONS

Cheng, X. et al., "Cell detection and counting through cell lysate impedance spectroscopy in microfluidic devices." Lab on a Chip 7, No. 6 (2007): 746-755.
(Continued)

*Primary Examiner* — Melissa Koval
*Assistant Examiner* — Courtney McDonnough
(74) *Attorney, Agent, or Firm* — HP Inc. Patent Department

(57) ABSTRACT

A microfluidic sensing device comprises a channel and an impedance sensor within the channel. The impedance sensor comprises a local ground and an electrode within the channel. The local ground and the electrode are to form an electric field region that is elongated along the channel.

16 Claims, 5 Drawing Sheets

(51) Int. Cl.
  G01N 27/12  (2006.01)
  B01L 3/00  (2006.01)
  G01N 15/12  (2006.01)
  G01N 15/10  (2006.01)
  G01N 15/14  (2006.01)

(52) U.S. Cl.
  CPC ......... *G01N 15/1031* (2013.01); *G01N 15/12* (2013.01); *G01N 15/1484* (2013.01); *G01N 27/12* (2013.01); *B01L 2200/10* (2013.01); *B01L 2300/0645* (2013.01); *G01N 2015/1006* (2013.01); *G01N 2015/1493* (2013.01)

(58) Field of Classification Search
  USPC .......................................................... 324/693
  See application file for complete search history.

(56) References Cited

U.S. PATENT DOCUMENTS

| | | |
|---|---|---|
| 6,426,615 B1 | 7/2002 | Mehta |
| 6,437,551 B1 | 8/2002 | Krulevitch et al. |
| 8,642,287 B2 | 2/2014 | Wang et al. |
| 8,795,497 B2 | 8/2014 | Sato et al. |
| 8,841,924 B2 | 9/2014 | Reccius et al. |
| 2002/0081228 A1 | 6/2002 | Hui et al. |
| 2003/0148530 A1 | 8/2003 | Lauks |
| 2004/0227529 A1 | 11/2004 | Brooks et al. |
| 2006/0062074 A1 | 3/2006 | Gundersen et al. |
| 2008/0221805 A1 | 9/2008 | Andrews |
| 2010/0006441 A1 | 1/2010 | Renaud et al. |
| 2010/0025246 A1 | 2/2010 | Cho et al. |
| 2010/0088039 A1 | 4/2010 | Yang et al. |
| 2011/0275111 A1 | 11/2011 | Pettigrew et al. |
| 2011/0279130 A1 | 11/2011 | Reccius et al. |
| 2012/0084022 A1 | 4/2012 | Giovangrandi et al. |
| 2012/0142032 A1 | 6/2012 | Morgan et al. |
| 2012/0168309 A1* | 7/2012 | Heikenfeld .......... G02B 26/004 204/518 |
| 2013/0085680 A1 | 4/2013 | Arlen et al. |
| 2013/0154671 A1 | 6/2013 | Lee et al. |
| 2013/0167621 A1 | 7/2013 | Lin et al. |
| 2013/0193003 A1 | 8/2013 | Reed et al. |
| 2013/0252234 A1 | 9/2013 | Nassef et al. |
| 2013/0258318 A1 | 10/2013 | Ayliffe |
| 2013/0313113 A1 | 11/2013 | Koser |
| 2014/0004501 A1 | 1/2014 | Talebpour et al. |
| 2014/0284221 A1 | 9/2014 | Liu et al. |

FOREIGN PATENT DOCUMENTS

| | | |
|---|---|---|
| TW | 200305717 A | 11/2003 |
| TW | 201224447 A | 6/2012 |
| WO | WO-2012064878 | 5/2012 |
| WO | WO-2012110922 | 8/2012 |
| WO | WO-2013117233 | 8/2013 |
| WO | WO-2014178827 | 11/2014 |
| WO | WO-2015116083 | 8/2015 |

OTHER PUBLICATIONS

Chin, et al., "Low-cost microdevices for point-of-care testing." In Point-of-care Diagnostics on a chip, pp. 3-21. Springer Berlin Heidelberg, 2013.

Claudel, J. et al., "Microfluidic biosensor for single cell high speed flow impedance spectroscopy." In Proceedings of the 8th International Conference on Sensing Technology, pp. 343-347. 2014.

International Search Report/Written Opinion, dated May 19, 2015, PCT Patent Application No. PCT/US2015/013825.

International Search Report/Written Opinion, dated Oct. 27, 2014, PCT Patent Application No. PCT/US2014/013748.

International Search Report/Written Opinion, dated May 21, 2015. PCT Patent Application No. PCT/US2015/013854.

Daniel Spencer et al: "Positional dependence of particles in microfludic impedance cytometry", Lab on a Chip, vol. 11, No. 7, Jan. 1, 2011 (Jan. 1, 2011), p. 1234, XP0551254.

Karen Cheung, Shady Gawad, and Philippe Renaud, Impedance Spectroscopy Flow Cytometry: On-Chip Labe-Free Cell Differentiation, ISAC Cytometry Part 1 65A, 2005.

Minerick, A.R., et al. "Manipulation and characterization of red blood cells with alternating current fields in microdevices". Nov. 6, 2003, Electrophoresis, 24(21), pp. 3703-3717.

* cited by examiner

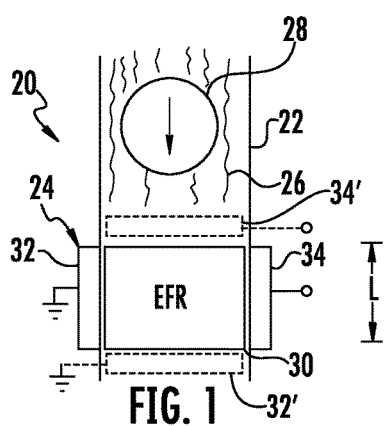
FIG. 1
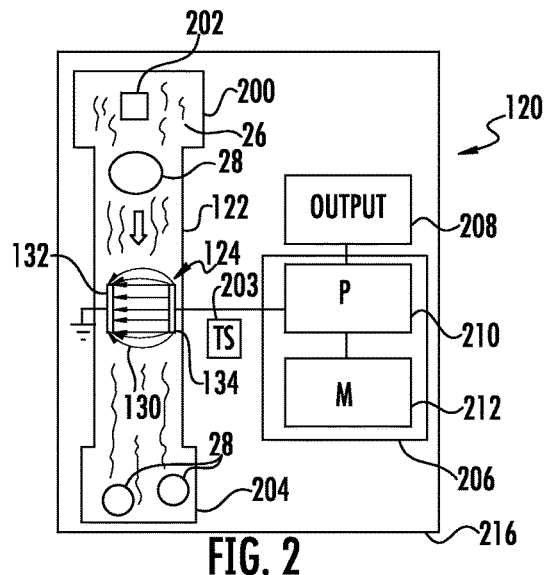
FIG. 2
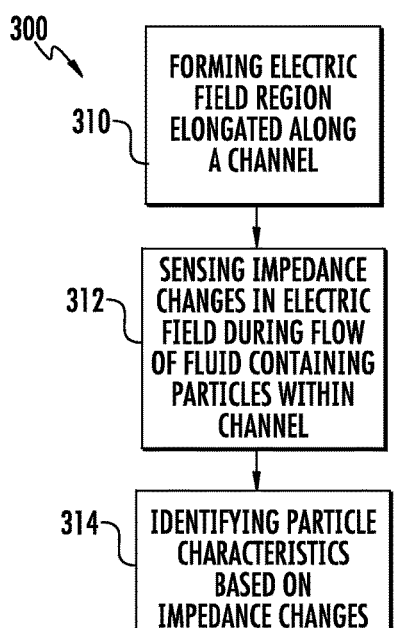
FIG. 3
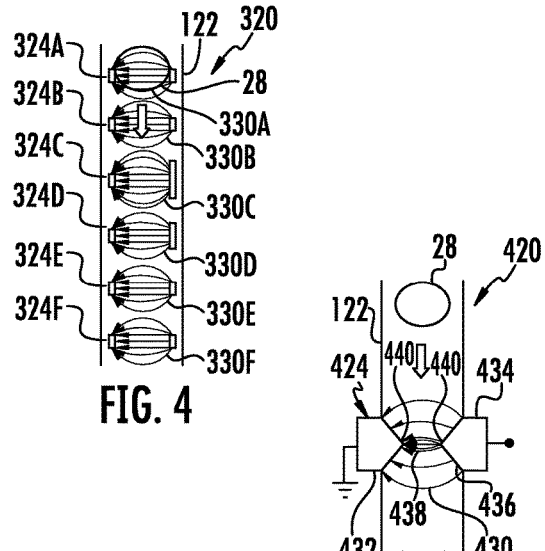
FIG. 4
FIG. 5

MICROFLUIDIC SENSING DEVICE

CROSS-REFERENCE TO RELATED APPLICATION

This application is a U.S. National Stage Application of and claims priority to International Patent Application No. PCT/US2014/013748, filed on Jan. 30, 2014, and entitled "MICROFLUIDIC SENSING DEVICE," which is hereby incorporated by reference in its entirety.

BACKGROUND

Some microfluidic sensing devices employ an impedance sensor to differentiate the size of cells or particles in flow cytometry applications. The impedance sensor relies upon signal magnitude. When a cell or particle is damaged, its dielectric properties may change, reducing the accuracy of such microfluidic sensing devices.

BRIEF DESCRIPTION OF THE DRAWINGS

FIG. 1 is a top view of an example microfluidic sensing system.

FIG. 2 is a top view of another example microfluidic sensing system.

FIG. 3 is a flow diagram of an example method that may be carried out by the system of FIG. 1 or the system of FIG. 2.

FIG. 4 is a top view of another example microfluidic sensing system.

FIG. 5 is a top view of another example microfluidic sensing system.

DETAILED DESCRIPTION OF THE EXAMPLE EMBODIMENTS

Figure 6:
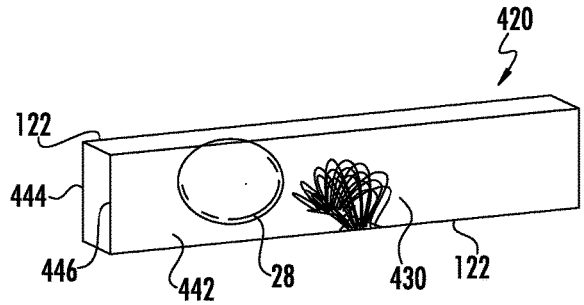
FIG. 6 is a perspective view of the microfluidic sensing system of FIG. 5.

FIG. 1 illustrates an example microfluidic sensing system 20. Microfluidic sensing system 20 utilizes an impedance sensor to sensor detect one or more characteristics of particles flowing across the impedance sensor. As will be described hereafter, microfluidic sensing system 20 provides enhanced sensing accuracy.

Microfluidic sensing system 20 comprises channel 22 and impedance sensor 24. Channel 22 comprises a microfluidic passage through which fluid 26 carrying one or more particles 28. For purposes of this disclosure, the term "microfluidic" refers to devices and/or passages which interact with fluids having a volume or carrying particles having dimensions in the "micro" range, microliter or micrometer, respectively. For purposes of this disclosure, the term "particle" encompasses any small minute piece, fragment or amount, including, not limited to, a biological cell or group of biological cells. A "fluid" may comprise a liquid, a gas or mixtures thereof. Channel 22 directs the flow of fluid 26 and particles 28 across or through an electric field region 30 (schematically illustrated) formed within channel 22 by impedance sensor 24. Examples of a fluid containing particles include but are not limited to, a blood sample and ink containing pigment/particles or the like.

Impedance sensor 24 forms electric field region 30 within channel 22. Impedance sensor 24 comprises a local electrical ground 32 and an electrode 34 which cooperate to form a region 30 of electric field lines that extend within channel 22 area. Electric ground 32 and electrode 34 are both "local" in that electric around 32 and electrode 34 are provided by electrically conductive contacts adjacent to the interior of channel 22 or in relatively close proximity to the interior of channel 22, such as just below or behind an interior surface or skin of channel 22. In contrast to a remote ground located outside of channel 22 or distant channel 22, a substantial majority, if not all, of the electric field region 30 between ground 32 and electrode 34 is contained within the interior of channel 22. As a result, the distance that the electric field lines between ground 32 and electrode 34 extend is not so long so as to reduce or weakens signal strength to a point that substantially impairs accuracy of system 20.

When particle 28 passes through electric field region 30, the electric field lines of region 30 are at least partially obstructed by particle 28 such that the electric field lines of region 30 are altered and travel around particle 28. The increased length of the electric field lines of region 30, resulting from having to travel around particle 28, increases or raises the electrical impedance that may be detected at electrode 34. As a result, the increase in impedance resulting from obstruction of electric field region 30 by particle 28 serves as an indicator of one or more characteristics of particle 28, such as the size of particle 28.

Ground 32 and electrode 34 of impedance sensor 24 are arranged or otherwise configured such that electric field region 30 is elongated along and within channel 22. In other words, the electric field region 30 extends in a direction along or parallel to the direction of channel 22 and parallel to the direction of flow of fluid 26 through channel 22 such that particle 28 interrupts or obstructs the electric field lines of electric field region 30 for a longer or prolonged period of time. As a result, the electrical signals representing changes in impedance as part of particle 28 flows through electric field region 30 have characteristic longer ramp ups and ramp downs, facilitating enhanced accuracy for the sensing of the size of particle 28.

FIG. 1 illustrates two alternative arrangements for ground 32 and electrode 34 for forming electric field region 30 which is elongated along channel 22. In a first arrangement, as indicated by solid lines, one or both of ground 32 and electrode 34 have major dimensions, length L, extending along the sides of channel 22 parallel to channel 22. In one implementation, ground 32 and electrode 34 are formed in sidewalls of channel 22. In another implementation, ground 32 and electrode 34 are both formed in one face or surface of channel 22, extending along or parallel to the sidewalls of channel 22. For example, in one implementation, ground 32 and electrode 34 are both formed in a floor of channel 22, each of ground 32 and electrode 34 extending along or adjacent to the sidewalls of channel 22.

In a second arrangement, as indicated by broken lines, ground 32' and electrode 34' are spaced from one another in a direction along channel 22. Electric field region 30 is elongated as a result of the upstream-downstream spacing of ground 32' and electrode 34'. In one implementation, both ground 32' and electrode 34'are formed on a same face or surface of the interior of channel 22. In other implementations, ground 32' and electrode 34' are formed on different surfaces along channel 22. Although ground 32'is illustrated as being downstream of electrode 34', this relationship may be reversed.

FIG. 2 is a diagram illustrating microfluidic sensing system 120, a particular implementation of microfluidic sensing system 20. As with microfluidic sensing system 20, microfluidic sensing system 120 utilizes an impedance sensor that produces an elongated electric field region along a channel to detect characteristics of particles are cells passing through the electric field region. Microfluidic sensing system 120 comprises source reservoir 200, pump 202, thermal sensor 203, channel 122, recipient reservoir 204, impedance sensor 124, controller 206 and output 208. Source reservoir 200 comprises a structure to receive a supply of fluid 26 containing particles 28. Source reservoir 200 communicates with channel 122 to supply fluid 26 and particles 28 for being driven or drawn through channel 122 across impedance sensor 124.

Pump 202 comprises a mechanism to move fluid 26 and particles 28 across impedance sensor 124. In the example illustrated, pump 202 drives fluid 26 and particles 28 from source reservoir 200 along channel 122 and across impedance sensor 124 towards recipient reservoir 204. In another implementation, pump 202 may alternatively be located within recipient reservoir 204 so as to draw fluid 26 and particles 28 from source reservoir 200 along channel 122 and across impedance sensor 124. Although one pump is illustrated, in other implementations, system 120 may include more than one pump.

In one implementation, pump 202 comprises a bubble jet pump, also referred to as a resistive or thermal inkjet (TIJ) pump in which a resistor is fired to a temperature so as to vaporize a portion of the liquid to form a bubble which drives surrounding liquid and particles. In such an implementation, the TIJ resistor serving as pump 202 may additionally serve as a heating device to heat system 120 to a prescribed temperature. In other implementations, pump 202 may comprise other types of pumps such as piezo element (PZT) pumps or other pumps having to a deflective membranes activated electrically, magnetically or mechanically.

Temperature sensor 203 comprises one or more temperature or thermal sensing devices to detect the temperature to which system 120 has been heated by the TIJ resistor also serving as a heating device or by another heating device or component independent of pump 202. Temperature sensor 203 is in communication with controller 206 and provides a closed loop feedback regarding the heating of system 120 by the TIJ resistive heater serving as pump 202 or an independent heating component.

Channel 122 directs fluid 26 and particles 28 from source reservoir 200 to recipient reservoir 204. Recipient reservoir 204 receives fluid 26 and particles 28 after particles 20 8/2 past across impedance reservoir 124. In some implementations, recipient reservoir 204 is connected to source reservoir 200, facilitating recirculation of fluid 26 and particles 28. In some implementations, channel 122 may additionally comprise one or more filters or other structures through which fluid 26 is to flow when passing from reservoir 200 to reservoir 204. In some implementations, system 120 may comprise multiple differently sized channels, wherein the different size of the channels are used to sort out and separate particles 28 of different size.

Impedance sensor 124 is similar to impedance sensor 24. Impedance sensor 124 comprises local ground 132 and electrode 134. Ground 32 and electrode 34 have major dimensions, length L, extending along the sides of channel 122 parallel to channel 122. In the example illustrated, ground 132 and electrode 134 are both formed in one face or surface of channel 22, extending along or parallel to the sidewalls of channel 122. In the example illustrated, ground 132 and electrode 134 are both formed in a floor of channel 22, each of ground 32 and electrode 34 extending along or adjacent to the sidewalls of channel 22. Because ground 132 and electrode 134 both formed in the floor of channel 122, the fabrication are formation of channel 122 with local ground 132 and electrode 134 may be less complex and less costly. Ground 132 and electrode 134 produce an elongated electric field region along a channel 122 for enhanced accuracy in detecting characteristics of particles 28 passing through the electric field region 130.

Controller 206 controls the operation of impedance sensor 124. Controller 206 regulates the supply of electrical charge to electrode 134 and controls the detection of impedance by sensor 124. In one implementation, controller 206 further controls the operation of the one of more pumps, such as pump 202 to control the flow of fluid 26 and particles 28 along channel 122. In one implementation, controller 206 additionally controls the heating a system 120 by the TIJ resistor of pump 202 or an independent heating component. Controller 206 comprises processing unit 210 and memory 212. For purposes of this application, the term "processing unit" shall mean a presently developed or future developed processing unit that executes sequences of instructions contained in a non-transitory memory or persistent storage device, such as memory 212. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 206 may be embodied as part of one or more application-specific integrated circuits (ASICs). Unless otherwise specifically noted, the controller is not limited to any specific combination of hardware circuitry and software, nor to any particular source for the instructions executed by the processing unit.

Output 208 comprises a device by which results from impedance sensor 124 are presented or otherwise made available or use in analyzing particles 28. In one implementation, output 208 comprises a port, signal transmitting contact or wireless transceiver or transmitter by which electrical signals representing the changes in impedance detected by sensor 124 are made available to external devices for analysis and use in identifying characteristics associated with particle 28. For example, in one implementation, output 208 may comprise a universal serial bus port by which impedance signals are transmitted to an external computing device or other host device such as a smart phone, tablet computer, laptop computer or the like for the determination of characteristics of particle 28, such as the size of particle 28. In one implementation, the results from the signals produced by impedance sensor 124 are stored in memory 212 for later retrieval and analysis by a host device.

In another implementation, memory 212 contains computer-readable instructions for directing processor 210 to determine one or more characteristics on-site from the impedance signals produced by impedance sensor 124. For example, in one implementation, memory 212 may contain code or instructions for directing processor 210 to determine or estimate the size of particle 28 based upon impedance signals from sensor 124 as particle 28 passes across electrical field region 130. In such an implementation, output 208 comprises a visual display or in auditory device to indicate the determined characteristic of particle 28, such as the determined size of particle 28. In some implementations, output 208 may additionally facilitate communication with a user of system 120 to provide instructions for the operation of system 120 or to provide confirmation or feedback regarding proper use of system 120 or completion of testing.

In one implementation, system 120 is implemented as a chip-based device supported on a single platform 216. In one implementation, platform 216 may be a handheld platform. As a result, system 120 may provide a microfluidic diagnostic system offering a configurable and mobile platform for point of care health diagnostics such as cell-based diagnostics for detecting infection diseases and chronic diseases.

In one implementation, platform 216 comprises a silicon substrate upon which an impedance measurement circuit is provided for operating and/or controlling electrode 134 to produce electric field region 130 for impedance sensing. In one implementation, the silicon substrate of platform 216 further supports circuitry for analyzing the sensed impedance signals to identify the one or more characteristics of particle 28. According to one implementation, the silicon substrate serving as platform 216 comprises a silicon chip having a size of between 0.5 mm$^2$ to 5 mm$^2$, wherein the silicon substrate supports each of the one or more TIJ resistors, serving as both pump 202 and a heater, the one of more impedance sensor electrodes 134 (and associated ground 132), and the one or more thermal sensors 203, in close proximity to one another upon the substrate with the associated circuitry. In one implementation, the silicon substrate supports each of the one or more TIJ resistors, serving as both pump 202 and a heater, the one of more impedance sensor electrodes 134 (and associated ground 132), and the one or more thermal sensors 203 at a spacing from one another of less than or equal to 5 mm and nominally at a spacing from one another of less than or equal to 0.5 mm.

In one implementation, platform 216 comprises a power supply. In another implementation, platform 216 is configured to be connected to a remote power supply. In one implementation, platform 216 and the componentry of system 120 are disposable. In such an implementation, the structures and components of system 120 may be fabricated using integrated circuit micro fabrication techniques such as electroforming, laser ablation, anisotropic etching, sputtering, dry and wet etching, photolithography, casting, molding, stamping, machining, spin coating, laminating, and so on.

FIG. 3 is a flow diagram of an example method 300 for sensing in determining particle characteristics based upon impedance changes. Method 300 may be carried out by either of impedance sensing system 20 or 120. As indicated by step 310, electrodes 34, 34', 134 are electrically charged so as to cooperate with local grounds 32, 32' and 132, respectively, to form electric field region 30, 130 that is elongated along channel 22, 122. As indicated by step 312, controller 206 senses impedance changes in electric field region 30, 130 during the flow of fluid 26 containing particles 28 within channel 22, 122. As indicated by step 314, controller 206 or a remote host device, utilizes a sensed impedance changes to identify one or more characteristics of particle 28, such as the size of particle 28. Because electric field region 30, 130 is elongated along channel 122, the time in which particle 28 reside within the electric field region 30, 130 is prolonged, enhancing signal reliability and detection accuracy.

FIG. 4 is a top view of microfluidic sensing system 320, an example implementation of microfluidic sensing system 20. Microfluidic sensing system 320 is similar to microfluidic sensing system 120 in that such a system 320 also comprises channel 122 as well as source reservoir 200, pump 202, recipient reservoir 204, controller 206, output 208 and platform 216, each of which are shown and described above with respect to system 120. In contrast to microfluidic sensing system 120, microfluidic sensing system 320 comprises impedance sensors 324A, 324B, 324C, 324D, 324E, 324F (collectively referred to as impedance sensors 324). Each of impedance sensor 324 similar to impedance sensor 124, forming an electric field region that is elongated along channel 122. In the example illustrated, impedance sensors 324 form differently sized or shaped electric field regions 330 along channel 122. In the example illustrated, impedance sensor 324D forms an electric field region 330 the that is larger than the electric field regions 330A, 330B, 330E and 330F formed by impedance sensors 324A, 324B, 324E and 324F, respectively. Impedance sensor 324C forms an electric field region 330C that is larger than the electric field region 330D. In the example illustrated, the larger electric field regions are provided by larger electrodes 134. In other implementations, the larger electric fields may be provided by larger local grounds 132 or both larger local grounds 132 and larger electrodes 134. The multiple impedance sensors 324 located along channel 122 produce signals having impedance spikes each time particle 28 passes across each of the impedance sensors 324. The difference signals produced by the multiple impedance sensor 324 are compared and statistically analyzed to identify the size of particle 28. For example, an average or median may be determined from signals from the multiple impedance sensors 324 to estimate a size of particle 28.

In the example illustrated in which some of the electric field regions 330 are provided with different sizes, size differentiation amongst particles is enhanced. Sufficiently large particles—particles larger than an electric field region, may saturate an electric field region 330. At the same time, particles that are small relative to an electric field region 330 may not result in a strong signal for determining impedance changes. Because system 320 forms differently sized electric field regions 330, the size of the electric field regions are customized to accommodate both smaller sized particles and larger sized particles while reducing inaccuracy brought about by large particle saturation of an impedance sensor and small particle weak signal strength.

In one implementation, controller 206 is configured to selectively and independently vary the frequency at which two or more of impedance sensors 324 are operated. For example, impedance sensor 324D may be operated a first frequency while impedance sensor 324E is operated at a second distinct frequency. By varying the frequency amongst the different impedance sensors 324, system 320 may analyze additional characteristics of particle 28. For example, in the case of biological cells, different frequencies may be utilized to differently excite the cytoplasm or the membrane of the cell. Such different excitation of different portion of the cell may result in a logical signals for the identification of additional characteristics associated with the cell or particle 28.

FIGS. 5 and 6 illustrate microfluidic sensing system 420, an example implementation of microfluidic sensing system 20. Microfluidic sensing system 420 is similar to microfluidic sensing system 120 in that system 420 also comprises channel 122 as well as source reservoir 200, pump 202, recipient reservoir 204, controller 206, output 208 and platform 216, each of which are shown and described above with respect to system 120. In contrast to microfluidic sensing system 120, microfluidic sensing system 420 comprises impedance sensor 424. Impedance sensor 424 forms a focused electric field region 430 across channel 122. Impedance sensor 424 comprises local ground 432 and electrode 434. Local ground 432 and electrode 434 extends along opposite surfaces of channel 122 and are separated by size varying gap 436. The term "size varying gap" refers to the distance across and between the opposing surfaces or faces of the local ground 432 and the opposite corresponding electrode 434, wherein the distance or size of the gap varies as one travels upstream or downstream along the channel 122. The size varying gap 436 results in the formation of electric field 430 having a focused center or core region 438 with a higher density of electric field lines within the narrowest portions of the gap. As a result, the electrical impedance signals produced by sensor 424 as particle 28 passes through electric field region 430 have a larger and sharper signal spike indicating how well particle 28 is blocking or obstructing electric field region 430. The larger or sharper signal spike produced by particle 28 passing through the focused field region 430 facilitates more reliable sensing of particle size.

In the example illustrated, gap 436 has a largest width substantially equal to the width of channel 122 and a smallest width W corresponding to the separation of opposing points 440 of ground 432 and electrode 434. Points 440 provide enhanced focus of the electric field lines extending therebetween. In one implementation, the width W between points 440 is tuned to accommodate the largest expected size of particles 28 which are to pass across electric field region 430. Although the largest width of gap 436 corresponds to the width of channel 122, in other implementations, the largest width of gap 436 may alternatively be less than the width of channel 122.

Although each of ground 432 and electrode 434 are illustrated as each being pointed, in other implementations, one of ground 432 and electrode 434 may alternatively comprise a flat bar having a surface parallel to the sides of channel 122. Although each of ground 432 and electrode 434 are illustrated as having a point 440 that is centered, in other implementations, ground 432 electrode 434 may have a point 440 that is asymmetric. For example, one or both of ground 432 and electrode 434 may alternatively have a configuration providing a gap that is widest closest to source reservoir 200 and that is narrowest closest to recipient reservoir 204. Although each of ground 432 and electrode 434 are both illustrated as having single points 440 opposite to one another, in other implementations, one or both of ground 432 and electrode 434 may alternatively have a series of points or jagged teeth along channels 122 or may be have curved surfaces that are convex or concave along channel 122.

As shown by FIG. 6, ground 432 and electrode 434 are formed along a single surface or face of channel 122. In the example illustrated, ground 432 and electrode 434 are both formed along the floor 442 of channel 122 extending from or adjacent to the opposing sidewalls 444, 446 of channel 122. Because ground 432 and electrode 434 are formed along the same face of channel number 122, such as floor 442, precise and reliable control of the spacing of points 440 and of gap 436 during manufacture is facilitated. Moreover, ground 432 and electrode 434 do not obstruct the cross-sectional area of channel 122 and the flow of fluid 26. In other implementations, ground 432 and electrode 434 are formed along and project from opposite surfaces within channel 122.

Figure 7:
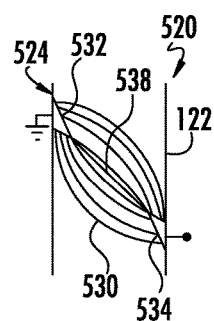
FIG. 7 is a top view of another example microfluidic sensing system.

FIG. 7 illustrates microfluidic sensing system 520, another example implementation of microfluidic sensing system 20. Micro-fluidic sensing system 520 is similar to microfluidic sensing system 420 except that microfluidic sensing system 520 comprises an impedance sensor 524 instead of impedance sensor 424. Those remaining components of system 520 are numbered similarly in FIG. 7 or are shown in FIG. 2.

Impedance sensor 524 is similar to impedance sensor 424 except that impedance sensor 524 comprises ground 532 and electrode 534 which cooperate to form an electric field region 530. Ground 532 and electrode 534 are similar to ground 432 and electrode 434 except that ground 532 and electrode 534 are spaced from one another along channel 122. In other words, one of ground 532 and electrode 534 is located upstream of the other of ground 532 and electrode 534. As a result, rather than generally extending perpendicularly across channel 122, electric field region 530 extends obliquely or diagonally across channel 122. The oblique orientation electric field region 530 increases the time during which a particle 28 passing across electric field region 530 obstructs electric field region 530. As a result, such obstruction of electric field region 530 results in longer ramp-up and ramp down times of the electric impedance signal, facilitating reliable and accurate detection of the size of the particle 28. As with impedance sensor 424, local ground 532 and electrode 534 are separated by a size varying gap across channel 122 to form a focused region 538 of electric field lines which produce a sharper impedance signal spike, further facilitating enhanced particle size detection.

Figure 8:
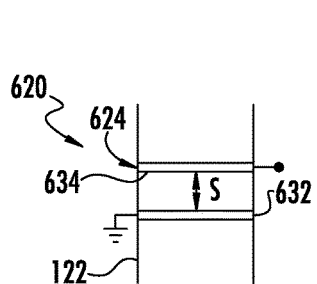
FIG. 8 is a top view of another example microfluidic sensing system.

FIG. 8 illustrates microfluidic sensing system 620, another example implementation of microfluidic sensing system 20. Microfluidic sensing system 620 is similar to microfluidic sensing system 120 in that system 620 also comprises channel 122 as well as source reservoir 200, pump 202, recipient reservoir 204, controller 206, output 208 and platform 216, each of which are shown and described above with respect to system 120. In contrast to microfluidic sensing system 120, microfluidic sensing system 620 comprises impedance sensor 624 which forms an elongated electric field region along channel 122 by spacing local ground 632 from electrode 634 along channel 122. In one implementation, local ground 632 and electrode 634 have a spacing S of between 2 μ and 5 μ, providing enhanced signal strength. In other implementations, ground 632 electrode 634 may have other spacings.

In the example illustrated, local ground 632 and electrode 634 comprise an electrically conductive surfaces or bars completely extending across channel 122 orthogonal to sides of channel 122. For example, in one implementation, local ground 632 and electrode 634 comprise exposed tantalum bars. In other implementations, the ground 632 and electrode 634 may be formed from other exposed or film covered electrically conductive materials or metals. In other implementations, one or both local ground 632 and electrode 634 may alternatively extend partially across channel 122. Although ground 632 is illustrated as being downstream of electrode 634, in other implementations, this relationship may be reversed.

Figure 9:
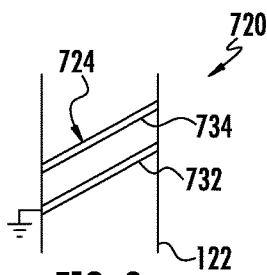
FIG. 9 is a top view of another example microfluidic sensing system.

FIG. 9 illustrates microfluidic sensing system 720, another implementation of microfluidic sensing system 20. Microfluidic sensing system 720 is similar to microfluidic sensing system 620 except that system 720 comprises impedance sensor 724 in lieu of impedance sensor 624. Impedance sensor 724 comprises local ground 732 and electrode 734 which are similar to ground 632 and electrode 634 of sensor 624 except that ground 732 and electrode 734 extend obliquely across or diagonally across channel 122. As a result, the elongated electric field region formed by ground 732 electrode 734, when electrode 734 is charged, obliquely extends across channel 122. Consequently, obstruction of electric field region by a particle 28 results in longer ramp-up and ramp down times of the electric impedance signal, facilitating reliable and accurate detection of the size of the particle 28.

Figure 10:
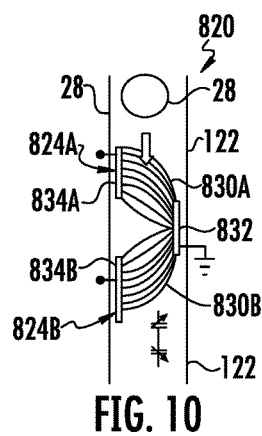
FIG. 10 is a top view of another example microfluidic sensing system.

FIG. 10 illustrates microfluidic sensing system 820, another implementation of microfluidic sensing system 20. Microfluidic sensing system 820 is similar to microfluidic sensing system 120 in that system 820 also comprises channel 122 as well as source reservoir 200, pump 202, recipient reservoir 204, controller 206, output 208 and platform 216, each of which are shown and described above with respect to system 120. In contrast to microfluidic sensing system 120, microfluidic sensing system 820 comprises a plurality of impedance sensors 824A and 824B (collectively referred to as impedance sensors 824) spaced along channel 122. Because system 820 comprises a plurality of impedance sensors 824, system 820 may determine the size of a particle 28 utilizing multiple signals which may be compared statistically analyzed to provide enhanced accuracy of the size detection of particle 28.

Impedance sensor 824A comprises local ground 832 and electrode 834A. Ground 832 and electrode 834A extend along opposite sides of channel 122 to form a diagonally extending electric field region 830A. Impedance sensor 824B comprises local ground 832 and electrode 834B. Ground 832 and electrode 834 extend along opposite sides of channel 122 to form a diagonally extending electric field region 830B downstream of electric field region 830A provided by impedance sensor 824A. As shown by FIG 10, sensors 824 share a single ground 832, reducing fabrication complexity. In addition, the diagonally extending electric fields 830 may enable sensors 824 to provide longer ramp up and ramp down signals when particle 28 passes across electric field regions 830 for enhanced size detection accuracy for particle 28.

In the example illustrated, impedance sensors 824 form differently sized or shaped electric field regions 830 along channel 122. In the example illustrated, impedance sensor 824B has a longer electrode 834B so as to form electric field region 830B that is larger than the electric field region 830A formed by impedance sensors 824A. As a result, size differentiation amongst particles is enhanced. Sufficiently large particles-particles larger than an electric field region, may saturate an electric field region 830. At the same time, particles that are small relative to an electric field region 830 may not result in a strong signal for determining impedance changes. Because system 820 forms differently sized electric field regions 830A, 830B, the size of the electric field regions are customized to accommodate both smaller sized particles and larger sized particles while reducing inaccuracy brought about by large particle saturation and small particle weak signal strength.

In one implementation, controller 206 (shown in FIG. 2) is configured to selectively and independently vary the frequency at which two or more of impedance sensors 824 are operated. For example, impedance sensor 824A may be operated a first frequency while impedance sensor 824B is operated at a second distinct frequency. By varying the frequency amongst the different impedance sensors 824, system 820 may analyze additional characteristics of particle 28. For example, in the case of biological cells, different frequencies may be utilized to differently excite the cytoplasm or the membrane of the cell. Such different excitation of different portion of the cell may result in a logical signals for the identification of additional characteristics associated with the cell or particle 28.

Although impedance sensors 824 are illustrated as comprising a pair of electrodes 834 sharing a single local ground 832, in other implementations, sensors 824 may alternatively comprise a pair of local grounds 832 sharing a single electrode 834. Although local ground 832 and electrodes 834 illustrated as being formed along channel 122 on the floor of channel 122, in other implementations, local ground 832 and electrode 834 (or electrode 834 and local grounds 832) may be formed on sidewalls of channel 122 or on both the floor and a sidewall of channel 122.

Figure 11:
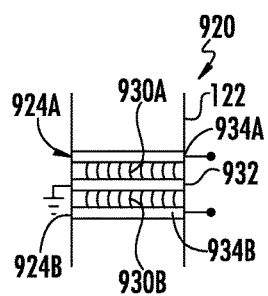
FIG. 11 is a top view of another example microfluidic sensing system.

FIG. 11 illustrates microfluidic sensing system 920, another implementation of microfluidic sensing system 20. Microfluidic sensing system 920 is similar to microfluidic sensing system 620 in that system 920 also comprises channel 122 as well as source reservoir 200, pump 202, recipient reservoir 204, controller 206, output 208 and platform 216, each of which are shown and described above with respect to system 120. In contrast to microfluidic sensing system 120, microfluidic sensing system 920 comprises a plurality of impedance sensors 924A and 924B (collectively referred to as impedance sensors 924) spaced along channel 122. Because system 920 comprises a plurality of impedance sensors 924, system 920 may determine the size of a particle 28 utilizing multiple signals which may be compared and statistically analyzed to provide enhanced accuracy for the size detection or estimation of particle 28.

Impedance sensor 924A comprises local ground 932 and electrode 934A. Ground 932 and electrode 934A are spaced along channel 122 upstream or downstream from one another. Impedance sensor 924B comprises local ground 932 and electrode 934B. Ground 932 and electrode 934B extend along channel 122 to form an electric field 930B downstream of electric field 930A provided by impedance sensor 924A. As shown by FIG. 11, sensors 924 share a single ground 932, reducing fabrication complexity.

In one implementation, electrode 934A is closer to ground 932 as compared to electrode 934B such that the electric field regions 930 formed by impedance sensors 924 are differently sized. As a result, particle 28 passing across such different electric field regions 930 may produce different impedance signals which may be compared and analyzed for enhanced size detection accuracy for particle 28.

Figure 12:
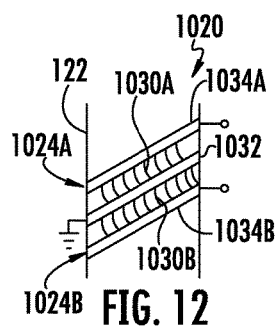
FIG. 12 is a top view of another example microfluidic sensing system.

FIG. 12 illustrates microfluidic sensing system 1020, another implementation of microfluidic sensing system 20. Microfluidic sensing system 1020 is similar to microfluidic sensing system 120 in that system 1020 also comprises channel 122 as well as source reservoir 200, pump 202, recipient reservoir 204, controller 206, output 208 and platform 216, each of which are shown and described above with respect to system 120. Microfluidic sensing system 1020 is also similar to microfluidic sensing system 920 except that the grounded pair of electrodes sandwiching the ground extend diagonally across channel 122.

As shown by FIG. 12, microfluidic sensing system 1020 comprises impedance sensor 1024A, formed by ground 1032 and electrode 1034A, and impedance sensor 1024B, formed by ground 1032 and electrode 1034B. Electrode 1034A and ground 1032 form electric field region 1030A while electrode 1034B and ground 1032 form electric field region 1030B. Electric field regions 1030 extend diagonally across channel 122. As a result, the impedance signals resulting from a particle 28 passing across electric field regions 1030 have longer ramp-up and ramp down times, facilitating enhanced size detection accuracy for particle 28. In one implementation, ground 1032 is equidistantly spaced from electrodes 1034. In another implementation, ground 1032 is differently spaced from electrodes 1034 to form differently sized electric field regions 1030 for enhanced size detection accuracy.

Figure 13:
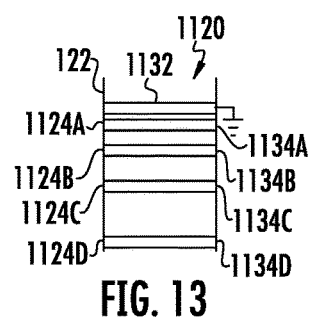
FIG. 13 is a top view of another example microfluidic sensing system.

FIG. 13 illustrates microfluidic sensing system 1120, another implementation of microfluidic sensing system 20. Microfluidic sensing system 1120 is similar to microfluidic sensing system 120 in that system 1120 also comprises channel 122 as well as source reservoir 200, pump 202, recipient reservoir 204, controller 206, output 208 and platform 216, each of which are shown and described above with respect to system 120. Microfluidic sensing system 1120 comprises a multitude of impedance sensors 1124A, 1124B, 1124C and 1124D (collectively referred to as sensors 1124) along channel 122. Sensors 1124A, 1124B, 1124C and 1124D share a single local ground 1132 and comprise electrodes 1134A, 1134B, 1134C and 1134D (collectively referred to as electrodes 1134), respectively.

Electrodes 1134 extend on one side of ground 1132 and are differently spaced from ground 1132. In addition, each of electrodes 1134 is separated from an adjacent electrode 1134 by a different spacing. For example, electrode 1134A and electrode 1134B are spaced from one another by a first distance along channel 122 while electrode 1134B and electrode 1134C are spaced from one another by a second greater distance along channel 122. The varying spacing between electrodes 1134 provides additional differentiation for signal comparison for determining the size of a particle 28 passing across the electric field regions formed by sensors 1124. In another implementation, electrodes 1134 may be equidistantly spaced from ground 1132.

Electrodes 1134 cooperate with local ground 1132 to form differently sized overlapping electric field regions. The differently sized electric field regions provided by sensors 1124 accommodate differently sized particles 28, maintaining signal strength or reducing the likelihood of an accuracy due to saturation by a larger sized particle 28. Although ground 1132 is illustrated as being upstream of electrodes 1134, in other implementations ground 1132 may be formed downstream of electrodes 1134. In some implementations, some of electrodes 1134 or additional electrodes 1134 may be provided upstream of ground 1132 to provide additional electric field reasons.

Figure 14:
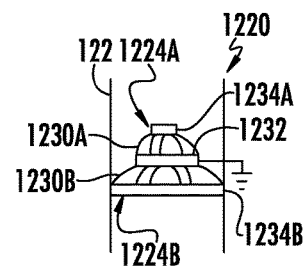
FIG. 14 is a top view of another example microfluidic sensing system.

FIG. 14 illustrates microfluidic sensing system 1220, another implementation of microfluidic sensing system 20. Microfluidic sensing system 1220 is similar to microfluidic sensing system 120 in that system 1220 also comprises channel 122 as well as source reservoir 200, pump 202, recipient reservoir 204, controller 206, output 208 and platform 216, each of which are shown and described above with respect to system 120. Microfluidic sensing system 1220 is similar to microfluidic sensing system 920 except that microfluidic sensing system 1220 comprises differently sized electrodes sandwiching and sharing and intermediate local ground. Microfluidic sensing system 1220 comprises impedance sensors 1224A and 1224B.

Impedance sensor 1224A comprises local ground 1232 and electrode 1234A. Ground 1232 and electrode 1234A are spaced along channel 122 upstream or downstream from one another. Impedance sensor 1224B comprises local ground 1232 and electrode 1234B. Ground 1232 and electrode 1234B extend along channel 122 to form an electric field region 1230B downstream of electric field region 1230A provided by impedance sensor 1224A. As shown by FIG. 14, sensors 1224 share a single local ground 1232, reducing fabrication complexity.

As further shown by FIG. 14, electrode 1234A has a shorter length as compared to electrode 1234B, extending across a smaller portion of channel 122. Electrodes 1234 cooperate with local ground 1232 to form differently sized electric field regions. The differently sized electric field regions provided by sensors 1224 accommodate differently sized particles 28, maintaining signal strength or reducing accuracy due to saturation by a larger sized particle 28. Although electrodes 1234 are illustrated as being equidistantly spaced from ground 1232, in other implementations, each of electrodes 1234 is differently spaced relative to ground 1232.

Figure 15:
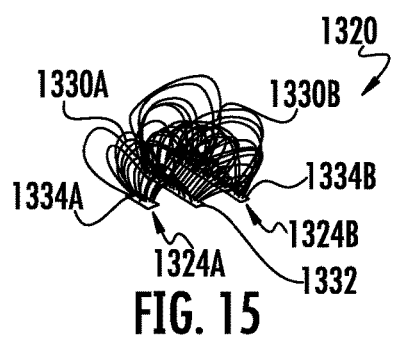
FIG. 15 is a perspective view of another example microfluidic sensing system.
Figure 16:
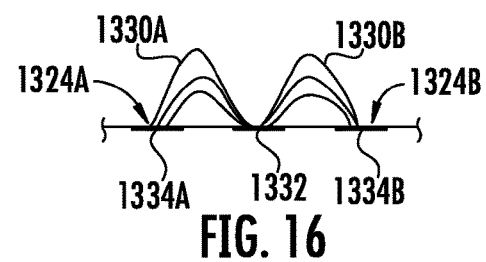
FIG. 16 is a side view of the microfluidic sensing system of FIG. 15.
Figure 17:
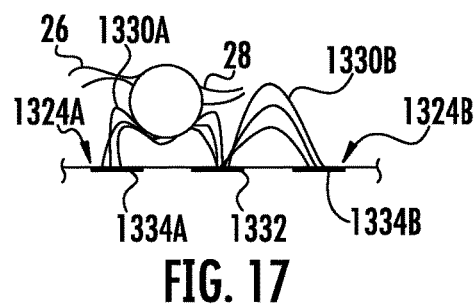
FIG. 17 is a side view of the microfluidic sensing system of FIG. 15 illustrating obstruction of an electric field region via particle.

FIGS. 15, 16, 17, and 18 illustrate microfluidic sensing system 1320 and its operation. Microfluidic sensing system 1320 is similar to microfluidic sensing system 1220 described above except that flow through channel 122 is in a reverse direction with impedance sensor 1324B and its electrode 1334B upstream of impedance sensor 1324A and its electrode 1334A. FIGS. 15 and 16 illustrate electric field regions 1330A and 1330B produced by impedance sensors 1324A and 1324B, respectively, in the absence of obstruction by particle 28. FIG. 17 illustrates an example obstruction of electric field region 1330A by particle 28 being carried by fluid 26. FIG. 17 illustrates how electric field lines must travel around particle 28, increasing impedance.

Figure 18:
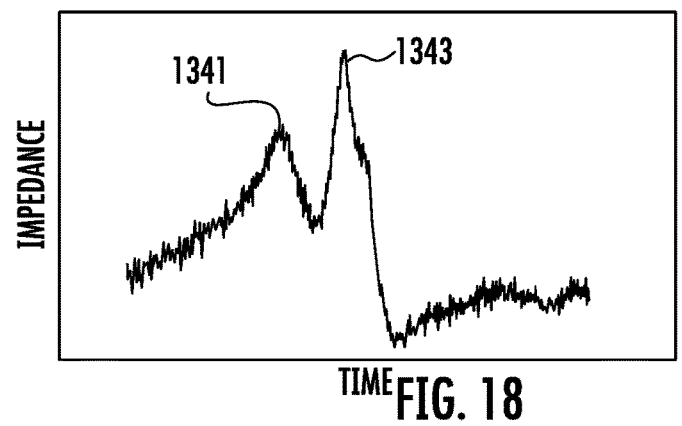
FIG. 18 is a graph of impedance over time during the passage of a particle across the microfluidic sensing system of FIG. 15.

FIG. 18 is a graph illustrating an impedance signal over time exhibited by microfluidic sensing system 1320 as particle 28 successively flows across the electric field regions 1330B and 1330A of impedance sensors 1324B and 1324A, respectively. As shown by FIG. 18, as particle 28 obstructs the larger electric field region 1330B to a first extent, the impedance signal produces a first spike 1341. As particle 28 continues to flow across the smaller electric field region 1330A, particle 28 obstructs the electric field region 1330A to a second greater extent due to its larger relative size with respect to electric field region 1330A. As a result, the impedance signal produces a second spike 1343 greater than the first spike 1341. The different sized impedance signal spikes may be compared and analyzed to ascertain or estimate the corresponding size of particle 28.

Figure 19:
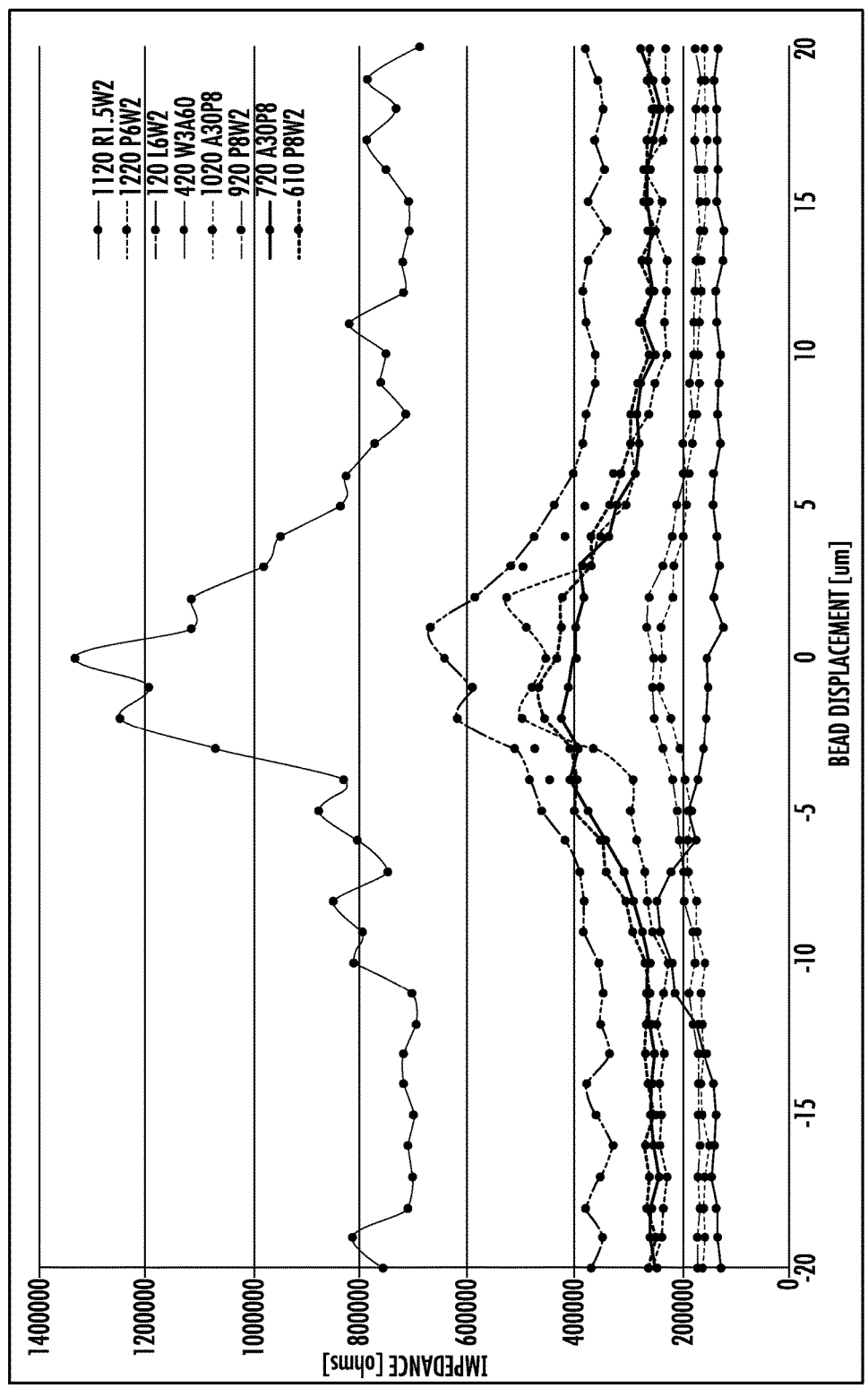
FIG. 19 is a graph impedance versus B displacement for the microfluidic sensing systems of FIGS. 2, 5, 8, 9, 12, 13 and 14.

FIG. 19 is a graph comparing impedance signals produced by different microfluidic sensing systems described above as a single sized particle flows across the one or more impedance sensors of each sensing system. As shown by FIG. 19, microfluidic sensing system 420 produced the strongest or largest impedance signal. Microfluidic sensing system 120 produced the next largest impedance signal.

Figure 20:
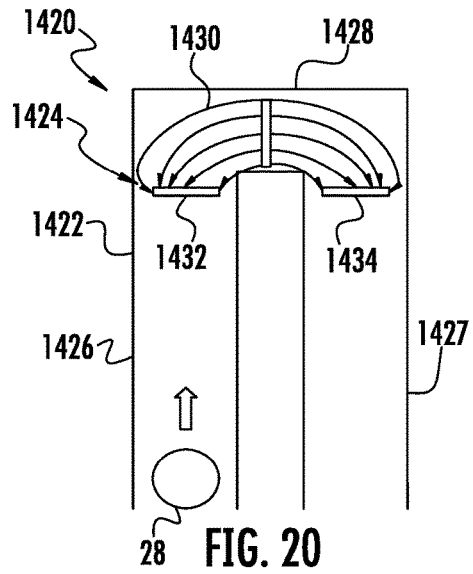
FIG. 20 is a top view of another example microfluidic sensing system.

FIG. 20 illustrates microfluidic sensing system 1420, another implementation of microfluidic sensing system 20. Microfluidic sensing system 1420 is similar to microfluidic sensing system 120 in that system 1420 also comprises source reservoir 200, pump 202, recipient reservoir 204, controller 206, output 208 and platform 216, each of which are shown and described above with respect to system 120. Microfluidic sensing system 1420 further comprises channel 1422 and impedance sensor 1424. Channel 1422 comprises a first portion 1426 extending from source reservoir 200 (shown in FIG. 2) a second portion 1427 extending to recipient reservoir 204 (shown in FIG. 2) and an intermediate bend 1428 connecting portions 1426 and 1427.

Impedance sensor 1424 comprises a local ground 1432 and an electrode 1434 located to form an electric field region 1430 which extends within and around bend 1428. The elongated electric field region 1430 is obstructed as particle 28 passes through bend 1428 and produces an impedance signal for the determination of the size of particle 28. Although ground 1432 is illustrated as being upstream electrode 1434, in other implementations, this relationship may be reversed.

Figure 21:
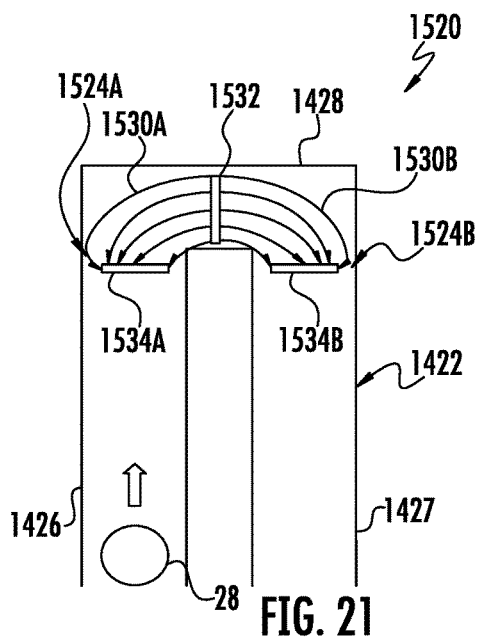
FIG. 21 is a top view of another example microfluidic sensing system.

FIG. 21 illustrates microfluidic sensing system 1520, another implementation of microfluidic system 20. Microfluidic sensing system 1520 is similar to microfluidic sensing system 1420 except the microfluidic sensing system 1520 comprises impedance sensors 1524A and 1524B (collectively referred to as impedance sensors 1524). Impedance sensor 1524 comprises local ground 1532 and electrode 1534A. Impedance sensor 1524B comprises local ground 1532 and electrode 1534B. Impedance sensors 1524 share a single ground 1532 and form elongated electric field regions 1530A and 1530B, respectively. The multiple impedance sensors provided by system 1520 provide multiple electrical field region obstructions by a particle 28 passing therethrough which may be compared and analyzed to facilitate enhanced size detection of particle 28. Although sensors 1524A and 1524B are asserted as sharing a single ground 1532, in other implementations sensors 1524 each have a dedicated local ground. In yet other implementations, sensing system 1520 may alternatively comprise impedance sensors having distinct local grounds that share a single electrode therebetween within bend 1428.

Figure 22:
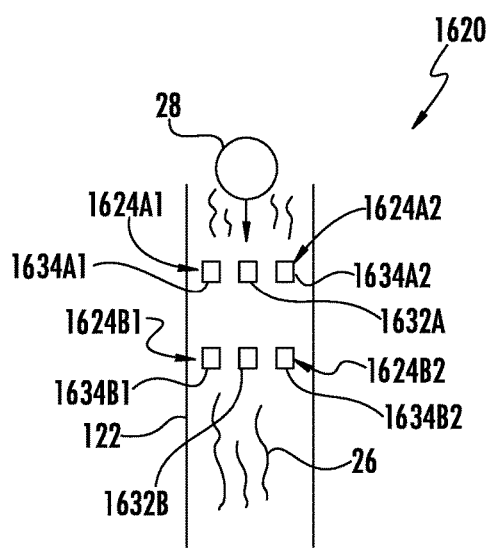
FIG. 22 is a top view of another example microfluidic sensing system.

FIG. 22 illustrates microfluidic sensing system 1620, another implementation of microfluidic sensing system 20. Microfluidic sensing system 1620 is similar to microfluidic sensing system 120 in that system 1620 also comprises channel 122 as well as source reservoir 200, pump 202, recipient reservoir 204, controller 206, output 208 and platform 216, each of which are shown and described above with respect to system 120. In contrast to microfluidic sensing system 120, microfluidic sensing system 1620 comprises an array of impedance sensors arranged across and along channel 122 for the detection of a size of a particle 28 carried by fluid 26 flowing through channel 122.

As shown by FIG. 22, microfluidic sensing system 1620 comprises local grounds 1632A, 1632B (collectively referred to as local ground 1632) and electrodes 1634A1, 1634A2, 1634B1 and 1634B2 (collectively referred to as electrode 1634). Grounds 1632 electrode 1634 clock rate with one to form an array of electric field regions across and along channel 122, wherein impedance signal resulting from the obstruction of the individual electric field regions further facilitates the ascertainment or estimating the size of particle 28.

In the example illustrated, local ground 1632A and the electrodes which are shared by local ground 1632A, electrodes 1634A1 and 1634A2 have a first size forming first sized electrical field regions. Local ground 1632B and electrodes which are shared by local ground 1632B, electrodes 1634B1 and 1634B2 have a smaller size forming second smaller sized electrical field regions. The differently sized electrical field regions as well as the different locations of the electrical field regions within channel 122 across channel 122 and along channel 122 enhance the accuracy of the estimation of the size of particle 28, accommodating differently sized particles 28 while maintaining signal strength and reducing the impact of saturation of electrical field region by a large particle 28.

Although microfluidic sensing system 1620 is illustrated as comprising an 2×2 array of impedance sensors 1624, in other implementations, microfluidic sensing system 1620 may comprise a larger array of impedance sensors. In some implementations, the array may comprise local grounds which are shared by electrodes downstream and/or diagonal to the local ground, forming diagonal electric field regions for the detection of particle 28. In yet other implementations, system 1620 may have a similar configuration, but where electrodes, rather than local grounds, are shared amongst multiple spaced local grounds forming the array of impedance sensors.

Figure 23:
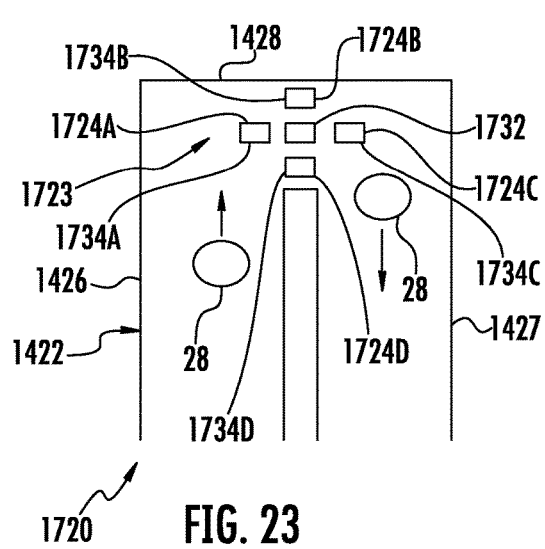
FIG. 23 is a top view of another example microfluidic sensing system.

FIG. 23 illustrates microfluidic sensing system 1720, another implementation of microfluidic sensing system 20. Microfluidic sensing system 1720 is similar to microfluidic sensing system 120 in that system 1720 also comprises source reservoir 200, pump 202, recipient reservoir 204, controller 206, output 208 and platform 216, each of which are shown and described above with respect to system 120. Microfluidic sensing system 1720 is similar to sensing system 1420 in that system 1720 comprises channel 1422. Microfluidic sensing system 1720 is similar to microfluidic sensing system 1620 in that system 1720 comprises an array 1723 of impedance sensors 1724.

As shown by FIG. 23, impedance sensors 1724 are formed in a floor of channel 1422 within bend 1428. In the example illustrated, impedance sensors 1724 comprise a shared single local ground 1732 and electrodes 1734A, 1734B, 1734C and 1734D spaced about local round 1732 and forming impedance sensors 1724A, 1724B, 1724C and 1724D, respectively. Similar to the impedance sensors of system 1620, impedance sensors 1724 form an array of electrical field regions which may be differently obstructed by the passage of particle 28 to produce impedance signals which may be analyzed to determine a corresponding estimates of the size of particle 28.

In addition to facilitating the detection of a size of a particle 28, microfluidic sensing system 1720 may be further used to facilitate the detection of a mass and density of particle 28. Because the momentum of a particle that is flowing around bend 1428 may impact which electric field region is obstructed by particle 28, the identification of an individual electric field region being obstructed by a particle 28 may further indicate the mass and therefore density of particle 28. Heavier particles will tend to flow to the outside of bend 1428 while lighter particles will tend to flow to the inside of bend 1428. For example, heavier or more dense particles 28 may flow through bend 1428 with greater momentum resulting in such particles 28 obstructing the electric field region of impedance sensor 1724B to a greater extent, producing a greater amplitude electrical impedance signal or spike, as compared to the extent to which such particles obstruct the electric field region of impedance sensor 1724D, producing a smaller amplitude electrical impedance signal or spike.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A microfluidic sensing device comprising:
a channel having
an impedance sensor within the channel, the impedance sensor comprising:
    a local ground within the channel; and
    an electrode within the channel, wherein the local ground and the electrode are to form an electric field region that is elongated along the channel;
a circuit to generate an electric field region using the electrode and the local ground of the impedance sensor;
a thermal inkjet (TIJ) resistor to move fluid and particles through the channel; and
a thermal sensor.

2. The microfluidic sensing device of claim 1, wherein the electrode is spaced from the local ground in a direction along the channel.

3. The microfluidic sensing device of claim 1, wherein at least one of the electrode and the local ground has a major dimension along the channel.

4. The microfluidic sensing device of claim 1, wherein the electrode faces oblique to the channel.

5. The microfluidic sensing device of claim 1 further comprising a second impedance sensor within the channel downstream the impedance sensor.

6. The microfluidic sensing device of claim 5, wherein the second impedance sensor comprises a second electrode and the local ground.

7. The microfluidic sensing device of claim 6, wherein the electrode is spaced from the local ground by a first distance and wherein the second electrode is spaced from the local ground by second distance different than the first distance.

8. The microfluidic sensing device of claim 5, wherein the impedance sensor and the second impedance sensor have different sized electric field regions.

9. The microfluidic sensing device of claim 5, wherein the channel comprises a first portion containing the electrode, a second portion containing the local ground and a bend connecting the first portion and the second portion, the bend containing the local ground.

10. The microfluidic sensing device of claim 1 further comprising a second impedance sensor transversely located relative to the impedance sensor within the channel.

11. The microfluidic sensing device of claim 1 further comprising:
a platform supporting the channel and the electrode and the local ground of the impedance sensor;
wherein the circuit is supported upon the platform;
the TIJ resistor is supported upon the platform within 5 mm of the impedance sensor; and
the thermal sensor is supported upon the platform within 5 mm of the impedance sensor and the TIJ resistor.

12. The microfluidic sensing device of claim 1, wherein the electrode and the local ground are separated by size varying gap across the channel.

13. A method comprising:
moving fluid containing particles within a channel of a sensing device using a bubble jet pump;
forming a first electric field region within the channel;
forming a second electric field region within the channel;
sensing impedance changes in the first electric field region and the second electric field region during flow of fluid containing particles within the channel, wherein the first electric field region and the second electric field region have different sizes; and
identifying particle characteristics based on the sensed impedance changes.

14. The method of claim 13, wherein the first electric field region and the second electric field region have different shapes.

15. A microfluidic sensing device comprising:
a platform supporting a channel;
an impedance sensor within the channel, the impedance sensor comprising a local ground and an electrode, wherein the electrode and the local ground are separated by size varying gap across the channel;
a circuit supported upon the platform to generate an electric field region using the electrode and the local ground of the impedance sensor;
a thermal inkjet (TIJ) resistor supported upon the platform within 5 mm of the impedance sensor; and
a thermal sensor supported upon the platform within 5 mm of the impedance sensor and the TIJ resistor.

16. A microfluidic sensing device comprising:
a platform supporting a channel;
an impedance sensor within the channel, the impedance sensor comprising a local ground and an electrode, wherein the local ground and the electrode are to form an electric field region that is elongated along the channel;
a circuit supported upon the platform to generate an electric field region using the electrode and the local ground of the impedance sensor; and
a piezo element pump supported upon the platform to move fluid and particles through the channel.

* * * * *